United States Patent [19]

Elson

[11] 4,202,334
[45] May 13, 1980

[54] CAP AND STOPPER

[75] Inventor: Edward E. Elson, Anaheim, Calif.

[73] Assignee: C. R. Bard, Inc., Murray Hill, N.J.

[21] Appl. No.: 882,233

[22] Filed: Feb. 28, 1978

[51] Int. Cl.$^2$ .............................................. A61J 1/00
[52] U.S. Cl. ................................... 128/272; 215/247; 215/355; 220/366
[58] Field of Search ........... 128/272, 221, 215, 218 R, 128/214 R, 247, 234, 224, 239; 215/296, 295, 355, 100 R, 247

[56] References Cited

U.S. PATENT DOCUMENTS

| 1,803,713 | 5/1931 | Langsner | 401/131 |
|---|---|---|---|
| 2,158,593 | 5/1939 | Scrimgeour | 128/221 |
| 2,320,323 | 5/1943 | Anunberg | 401/129 |
| 2,638,897 | 5/1953 | Poitras | 128/221 |
| 2,849,739 | 9/1958 | Dresden | 401/128 |
| 3,055,361 | 9/1962 | Ballard | 128/221 |
| 3,118,557 | 1/1964 | Bogikes | 215/247 |
| 4,046,145 | 9/1977 | Choksi | 128/215 |

FOREIGN PATENT DOCUMENTS

| 1028524 | 5/1953 | France | 128/218 R |
|---|---|---|---|
| 1398704 | 4/1965 | France | 401/129 |

Primary Examiner—Robert W. Michell
Assistant Examiner—Milford A. Juten
Attorney, Agent, or Firm—Spensley, Horn, Jubas & Lubitz

[57] ABSTRACT

A combination cap and stopper for sealing a substance within a syringe whether the needle remains on the syringe or is removed, consisting of a rubber or plastic device having a generally cylindrical portion and a portion having a generally frustoconical shape. The cylindrical portion has a frustoconical axial bore therein with an axially extending groove formed in the frustoconical wall and at the bottom end of the bore a plug-like cylindrical protrusion. The portion of generally frustoconical shape being solid and having a raised target on its base so as to aid in proper insertion of a cannula.

7 Claims, 3 Drawing Figures

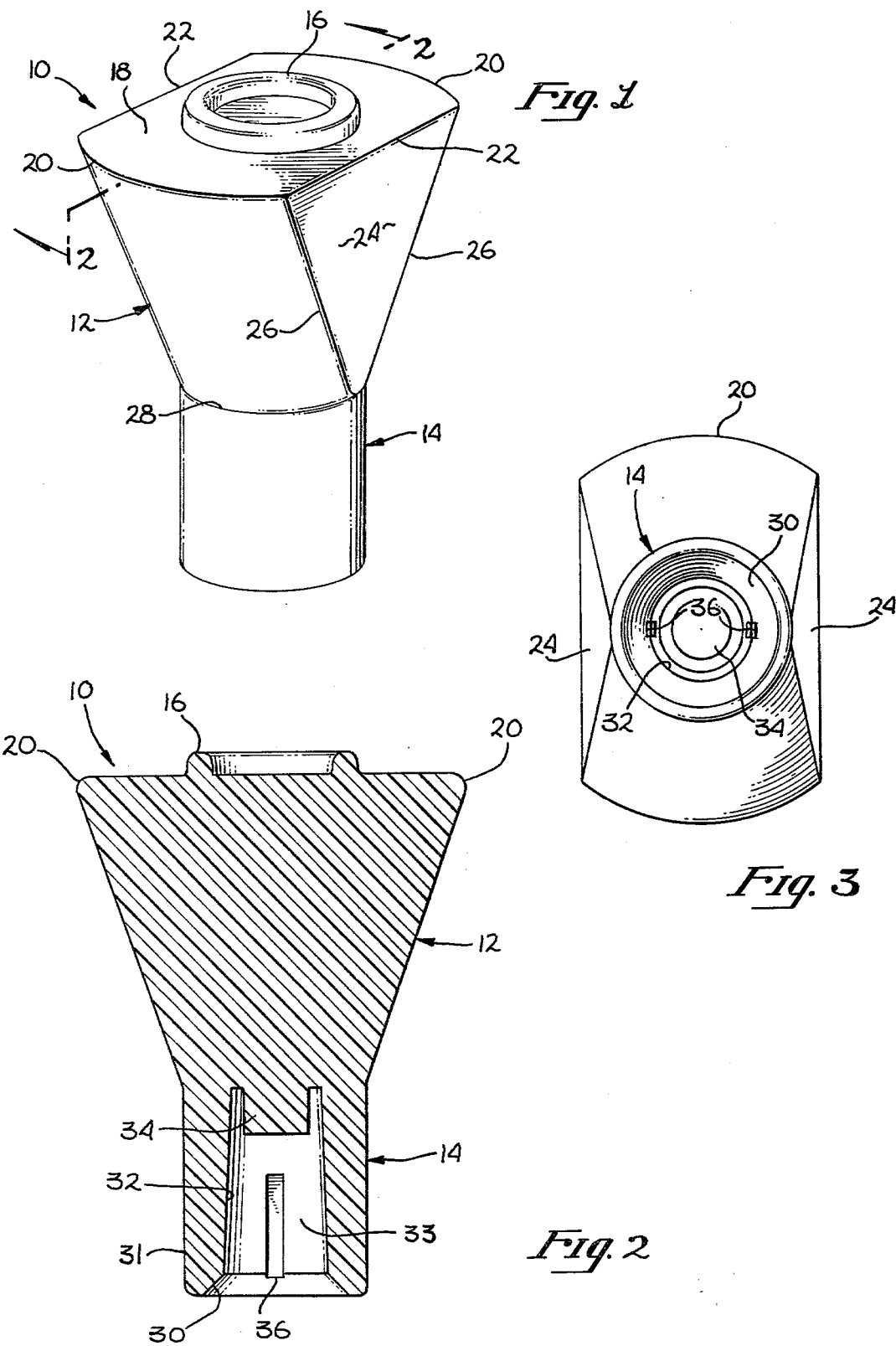

CAP AND STOPPER

BACKGROUND OF THE INVENTION

1. Field of the Invention

This invention relates generally to devices for sealing a substance within a syringe and particularly to capping and stopping means.

2. Prior Art

Two devices have long been used to seal a syringe which contains a sample which must be kept free from contamination and prevented from escaping the syringe. The first device is a simple solid frustoconical shaped stopper made of rubber, plastic or other material which may be easily pierced by a cannula. The cannula is inserted into the stopper a distance sufficient to insure that it is secure therein and that the cannula is sealed. The second device is a cap. The cap is used to seal the open end of the syringe after the cannula assembly has been removed. The cap is typically made of an elastic material which must be somewhat stretched to fit over the end of the syringe. Pertinent Prior Art patents include U.S. Pat. No. 3,098,481 to Wikander et al and U.S. Pat. No. 3,380,452 to Elias.

Kits or trays are in common usage in conjunction with the collection of samples by syringe. Such kits must contain both a cap and a stopper since very often the preference for the specific sealing means is not readily discernable in advance. This means that the kit or tray must have space for both sealing means, and both sealing means must be kept in inventory.

The typical stopper is a solid conical section having two flat parallel ends which are perpendicular to the main axis of the conical section, i.e. frustoconical. Such stoppers, having all rounded sides, are difficult to hold and thus the cannula is often inserted at an improper angle which may result in the cannula puncturing a finger of the technician.

The typical cap is rather small, having a diameter not much larger than the outer diameter of the cylindrical portion of the syringe. The cap is therefore somewhat difficult to hold and place over the end of the syringe and in any event will trap air in the syringe thereby contaminating the sample contained therein.

It is therefor an object of the present invention to provide a cap and stopper of unitary construction thereby eliminating the necessity of providing space on the tray for a cap and another space for a stopper; and also eliminating the necessity of keeping both caps and stoppers in inventory.

It is another object to provide an improved cap and stopper as above having relatively large flat surfaces so as to provide for improved gripping and so as to prevent the device from rolling about on a tabletop or other flat surface when accidentally (or purposefully) impacted.

It is a further object of the present invention to provide an improved cap and stopper which has a target area on the stopper portion to aid in proper selection of a location to insert the cannula.

A further object of this invention is to provide a cap which will allow air to be expelled from the cap during the capping process rather than compress air from the cap into the syringe thereby contaminating the sample.

Another object of this invention is to provide a cap of a material sufficiently soft and flexible such that the cap will properly seal the end of the syringe whether it is a threaded end or a tapered end without threads.

SUMMARY OF THE INVENTION

The device of the present invention is a combination cap and stopper of unitary construction used for sealing a sample inside a syringe. The stopper portion of the device is a solid having a generally frustoconical shape. The stopper portion is provided with two opposing parallel flat surfaces which are generally parallel to the axial centerline of the stopper. The base of the stopper is provided with a target, formed of a bead of the same material of which the stopper is made, which serves to guide the insertion of a cannula into the stopper. The cap portion consists of a cylindrical extension of the opposite base of the stopper with its centerline coincident with the centerline of the stopper. The cap portion has an axially extending frustoconical bore having a centerline which is also coincident with the centerline of the stopper. The frustoconical tapered bore has a tapered mouth to aid insertion of the syringe. The wall of the frustoconical bore and the bottom of the frustoconical bore are provided with a groove and a cylindrical plug respectively, to allow air to escape from the cap and to form a positive seal on the syringe between the plug and the interior cylindrical wall of the syringe.

BRIEF DESCRIPTION OF DRAWINGS

FIG. 1 is a perspective of the combination cap and stopper of the present invention.

FIG. 2 is a sectional view taken along the line 2—2 of FIG. 1.

FIG. 3 is a bottom view.

DETAILED DESCRIPTION OF THE INVENTION

The improved cap and stopper of the present invention 10 are integrally formed of a single mass of rubber, or other material such as a plastic, as shown in the accompanying figures.

FIG. 1 is a perspective view used to particularly illustrate the features of the stopper portion 12 of the present invention 10. The stopper portion is basically frustoconical having a base 18 on which is located a target 16. Typically, the target 16 is composed of a bead of material, identical to that of which the stopper is made, formed in the shape of a ring. The target 16 indicates to a technician the optimum area for insertion of the cannula for best sealing. The target may also be comprised of a groove, appropriate painted markings, or even a raised area of the base 18.

The base 18 has a plurality of arcuate portions 20 and a plurality of straight portions 22. The straight portions are defined by the intersection of the base 18 with a plurality of generally flat surfaces 24. These flat surfaces 24 are further defined by the edges 26 and extend substantially to the interface 28 of the stopper 12 and cap 14. Surfaces 24 are symmetrically spaced about the axis of the stopper and lie in a plane approximately parallel to the axis of the stopper. As is clearly shown in FIGS. 2 and 3, the stopper 12 and its various surfaces extend radially outward from the cap 14. The flat surfaces serve as a sure and convenient means to grip the device and also prevent the device from rolling about the base 18, when placed on a flat surface, due to accidental (or intentional) impacts.

FIG. 2 is a cross sectional view taken along the line 2—2 of FIG. 1. This view serves primarily to illustrate the features of the cap portion 14 of the present invention 10. The cap portion 14 is of cylindrical shape defined by the exterior cylindrical wall 31 and the interior frustoconical wall 32. The interior wall 32 is tapered so as to form an axially extending bore 33 in the cap portion which at its closed end is of a diameter less than its diameter adjacent the mouth 30 of the bore. The mouth 30 is gradually tapered inward from the exterior wall 31 to the interior wall 32. At the closed end of bore 33 is formed a cylindrical plug 34 the base of which is slightly spaced from the interior wall 32. The plug extends axially toward the mouth 30 of bore 33. A groove 36 located in the interior wall 32 extends axially from the mouth 30 toward the closed end of the bore 33.

The tapered mouth 30 aids in insertion of the end of a syringe into the bore 33 of cap 14. During insertion of the end of the syringe, the grooves 36 allow the air trapped in the bore to escape from the cap 14 rather than be compressed into the syringe and contaminate the sample. In the preferred embodiment at least two grooves 36 are disposed within the cap 14. As the syringe is inserted further into the frustoconical bore the diameter of the bore 33 gradually decreases causing the cap 14 to grip the syringe tighter thereby insuring an effective seal of the syringe. As the syringe is inserted further into the bore 33, the plug 34 passes into the syringe and contacts the interior wall of the syringe thereby forming a positive seal of the end of the syringe. The frustoconical bore 33 seals on the exterior surface of the syringe and the plug 34 seals on the interior cylindrical surface of the syringe.

FIG. 3 is an end view used to more clearly illustrate the form of surfaces 24 and the proportions and shape of the unitary cap and stopper 10.

There has thus been provided an improved cap and stopper device of unitary construction which is easy to grip and will not roll about on a flat surface when impacted. The cap portion allows air to escape therefrom during insertion of a syringe rather than compressing the air into and thereby contaminating the sample within the syringe. It is therefore no longer necessary to inventory two separate items, i.e. caps and stoppers, and only one space need be provided on syringe kit trays.

Having thus described the invention it is obvious that numerous modifications and equivalent devices may be made by those skilled in the art without departing from the spirit and scope of the invention. For example while plug 34 has a generally cylindrical shape, other configurations are within the scope of the present invention so long as such element fits up into the syringe tip. It is thus intended that the breadth of the invention be limited only by the spirit and scope of the appended claims.

What is claimed is:

1. A device for sealing a sample within a syringe comprising a cap means and stopper means of unitary construction:
    said cap means having an interior frustoconical wall and an exterior cylindrical wall, a closed end and a mouth, said interior wall configured to engage an exterior wall of said syringe as said syringe and cap means are joined together;
    said cap means being provided with a first means for allowing air to escape from the cap during insertion of said syringe into said cap means;
    said cap means being further provided with a second means for forming a seal with an interior wall of the syringe as the syringe approaches the closed end of said cap means; and
    said stopper means having a base integrally joined to said cap means and a plurality of generally flat surfaces extending radially outward on said stopper means adjacent said base, said stopper means configured such that the syringe is substantially prevented from rolling about its axis on a flat surface when said device is joined thereto, and wherein the cross-sectional area of said stopper means adjacent said base is greater than the cross-sectional area of said cap means.

2. The device according to claim 1 wherein said first means comprises a groove in the interior frustoconical wall of said cap means.

3. The device according to claim 1 wherein said second means comprises a cylindrical plug located at the closed end of said cap means, extending from said closed end toward the mouth of said cap means.

4. The device according to claim 1 wherein said stopper means is provided with a target.

5. A device for sealing a sample within a syringe comprising a cap and a stopper of unitary construction:
    said cap having an interior frustoconical wall and an exterior cylindrical wall, a closed end and a mouth, said interior wall configured to engage an exterior wall of said syringe as said syringe and cap are joined together;
    said cap further having first and second grooves disposed along said interior frustoconical wall, said grooves communicating with said mouth, and wherein said closed end of said cap is provided with a cylindrical plug which engages and forms a seal with an interior wall of the syringe as said syringe and said cap are joined together;
    said stopper having a target area formed thereon, a base joined to said cap and a plurality of generally flat surfaces extending radially outward on said stopper adjacent said base and configured such that the syringe is substantially prevented from rolling about its axis on a flat surface when the device is joined to the syringe, and wherein the cross-sectional area of said stopper adjacent said cap is greater than the cross-sectional area of said cap.

6. A device for sealing a sample within a syringe comprising:
    a cap having an interior frustoconical wall configured to engage an exterior wall of said syringe as said cap and syringe are joined together;
    groove means disposed in said wall for allowing air to escape from said cap as said cap and syringe are joined together;
    sealing means provided on said cap for forming a seal with an interior wall of said syringe; and
    a stopper having a base integrally joined to said cap and a plurality of surfaces extending radially outward on said stopper adjacent said base and configured to prevent the syringe from rolling about its axis on a flat surface when the device is joined thereto to the syringe and wherein the cross-sectional area of said stopper adjacent said cap is greater than the cross-sectional area of said cap.

7. A device according to claim 6 wherein said seal means comprises a cylindrical plug.

* * * * *